(12) United States Patent
Gibson et al.

(10) Patent No.: US 8,526,001 B2
(45) Date of Patent: Sep. 3, 2013

(54) VERSATILE SURFACE PLASMON RESONANCE ANALYZER WITH AN INTEGRAL SURFACE PLASMON RESONANCE ENHANCED FLUORESCENCE MODE

(71) Applicant: Ciencia, Inc., East Hartford, CT (US)

(72) Inventors: George N. Gibson, Storrs, CT (US); Ernest F. Guignon, Canton, CT (US); Michael T. Reilly, Manchester, CT (US)

(73) Assignee: Ciencia, Inc., East Hartford, CT (US)

( * ) Notice: Subject to any disclaimer, the term of this patent is extended or adjusted under 35 U.S.C. 154(b) by 0 days.

(21) Appl. No.: 13/751,181

(22) Filed: Jan. 28, 2013

(65) Prior Publication Data

US 2013/0169954 A1 Jul. 4, 2013

Related U.S. Application Data

(63) Continuation of application No. 12/545,656, filed on Aug. 21, 2009, now Pat. No. 8,368,897.

(60) Provisional application No. 61/189,779, filed on Aug. 22, 2008.

(51) Int. Cl.
*G01N 21/55* (2006.01)

(52) U.S. Cl.
USPC ....... 356/445; 356/446; 435/288.7; 435/7.91; 435/7.1; 436/525

(58) Field of Classification Search
USPC ................. 356/445–446; 359/809; 436/525; 435/7.1, 7.92, 288.7
See application file for complete search history.

(56) References Cited

U.S. PATENT DOCUMENTS

| | | | |
|---|---|---|---|
| 4,931,384 A | 6/1990 | Layton et al. | |
| 6,493,097 B1 * | 12/2002 | Ivarsson | 356/630 |
| 6,600,563 B1 | 7/2003 | Bahatt et al. | |
| 6,731,388 B1 | 5/2004 | Simon et al. | |
| 6,873,417 B2 | 3/2005 | Bahatt et al. | |
| 6,982,819 B2 | 1/2006 | Sawin et al. | |
| 7,057,786 B2 | 6/2006 | Sawin et al. | |
| 7,251,085 B2 | 7/2007 | Bahatt et al. | |
| 7,349,080 B2 | 3/2008 | Aklian | |
| 7,835,076 B2 | 11/2010 | Roorda et al. | |
| 8,111,400 B2 * | 2/2012 | Ran et al. | 356/445 |
| 2007/0057211 A1 * | 3/2007 | Bahlman et al. | 250/584 |

* cited by examiner

*Primary Examiner* — Gregory J Toatley
*Assistant Examiner* — Iyabo S Alli
(74) *Attorney, Agent, or Firm* — Alix, Yale & Ristas, LLP

(57) ABSTRACT

An instrument for measuring and analyzing surface plasmon resonance on a sensor surface has a polarized light source optically connected to the sensor surface by a plurality of optical elements, including in one embodiment an optical telescope that transfers light from a rotatable reflecting surface to the sensor surface. Selective positioning of a cylindrical lens into a first position within the path of light transforms collimated light to a rectangular wedge that is incident upon the sensor surface at numerous angles. In another embodiment, the light source is operated as a laser to excite fluorescence on the sensor surface and the fluorescence is selectively directed to a detector by appropriate optical elements positioned in specific configurations.

15 Claims, 5 Drawing Sheets

Sectional View of Filter Assembly in GCSPRI Mode

Fluidics Diagram

VERSATILE SURFACE PLASMON RESONANCE ANALYZER WITH AN INTEGRAL SURFACE PLASMON RESONANCE ENHANCED FLUORESCENCE MODE

RELATED APPLICATION

This application is a continuation of U.S. patent application Ser. No. 12/545,656 for "Versatile Surface Plasmon Resonance Analyzer With an Integral Surface Plasmon Resonance Enhanced Fluorescence Mode," filed Aug. 21, 2009, which claims priority from U.S. Provisional Patent Application No. 61/189,779, filed Aug. 22, 2008, the entire contents of each of which are hereby incorporated by reference.

STATEMENT REGARDING FEDERALLY SPONSORED RESEARCH

This application is based on research and development done under NIH/NIGMS Grant No. 2R44GM075407-02 and NIH/NIDDK Grant No. IR43DK077291.

TECHNOLOGICAL FIELD

The described embodiments relate to an instrument and method for the detection and measurement of a wide variety of specific molecules and biological cells.

BACKGROUND

Optical techniques that identify and measure biological cells and macromolecules frequently require fluorescent or enzymatic labels as well as a means of isolating or separating analytes. Surface plasmon resonance ("SPR") techniques separate analytes contained in complex mixtures through the use of specific capture ligands, usually antibodies, bonded to a metallic surface in contact with a dielectric. Light of a specific wavelength striking the metal/dielectric interface at a specific angle can support a rapidly decaying wave phenomenon (surface plasmon) if there is a means of matching the momentum (K-vector) of the light with that of the loosely bound electrons at the metal/dielectric interface. When this resonance energy transfer occurs, the intensity of the light reflected from the metal surface decreases markedly. This resonance phenomenon is quite sharp—on the order of a few millidegrees—and the incident angle is extremely sensitive to the refractive index at the surface of the metal substrate. In the present case, a diffraction grating immediately below a thin layer of metal provides the momentum matching mechanism.

Typically, antibodies bound to the metal surface are used to capture specific analyte molecules present in a complex sample mixture which flows over the metal surface. This highly specific immunochemical process results in specific analyte molecules being bound to well-identified regions of the metal substrate without the necessity of physical compartmentalization of the fluid. For each captured analyte, the magnitude of the change in the resonant angle is proportional to the mass of analyte captured in each region.

With appropriately designed accommodations, an SPR analyzer can be made to capture living cells by surface antigens normally expressed on the surface of the cells. In this manner, specific cell types, distinguished by their surface antigens can be isolated and captured on a metal surface. Cells captured in an SPR analyzer in this manner can be activated by contact with suitable mitogens.

Capture antibodies for various cell secretions (cytokines) can be spotted on the surface in order to immobilize the secreted cytokines. Cytokines are relatively small molecules and the amount of a particular cytokine secreted by a single cell is typically too small to be detected by SPR resonance angle shifts.

It has been observed that energy from surface plasmons can be out-coupled and absorbed by fluorophore molecules in close proximity to the metal surface (see Lakowicz, J. R., 2006, "*Plasmonics in Biology and Plasmon-Controlled Fluorescence*", DOI 10.1007/s 11468-005-9002-3). The local field of the propagating wave at the metal/dielectric boundary enhances absorption of plasmons as compared to free-space absorption. The subsequent fluorescent emission is out-coupled into free-space propagating lobes in accordance with the momentum matching conditions previously described. Fluorescence generated in this manner is emitted as directional lobes rather than omnidirectionally as in solution (i.e., as in a typical fluorometer). An optical detection system can be designed to capture directionally emitted fluorescence with much greater efficiency than can be done with omnidirectional fluorescence in a fluorometer. This enhanced capture efficiency results in considerably greater detection sensitivity and is sufficient to quantitatively measure cytokine secretion from single cells (see Reilly, M. T. et al. 2005, "*SPR Surface Enhanced Fluorescence with a Gold-Coated Corrugated Sensor Chip*" SPIE 6099-14TR, the entire disclosure of which is hereby incorporated by reference).

SUMMARY

An analytical instrument facilitates the immunochemical capture of specific living cells and/or macromolecules on the surface of a grating-coupled surface plasmon resonance "chip" where quantitative measurement of the cells and/or macromolecules is performed by means of surface plasmon resonance in either of two operating modes.

The instrument provides three selectable "modes" of operation: First, a "scanning mode" in which the angle of collimated polarized light is varied; second, a "non-scanning mode" in which a wedge of non-collimated light containing the resonant angle is focused on the chip by means of an optical system; and third, an "SPR-enhanced fluorescence mode", wherein smaller captured molecules are labeled with a fluorophore and quantitatively measured by surface plasmon enhanced fluorescence.

The instrument provides a means of monitoring cellular responses in real time, and provides a sensitive means of quantitatively measuring and identifying cell products. The instrument has been demonstrated to process over 1000 capture sites simultaneously without crosstalk.

DETAILED DESCRIPTION

As used herein, the term "dithering" refers to a process of averaging between pixels of different colors to result in a smoother blended transition between the edge of two areas. The acronym "GCSPRI" stands for Grating-coupled Surface Plasmon Resonance Imaging. The term "telescope" refers to an optical configuration for relaying an image from one plane to another plane.

A grating-coupled surface plasmon resonance analyzer selectively operates in scanning and non-scanning GCSPRI modes, and also provides an integral SPR-enhanced fluorescence mode with sensitivity extending into the femptomolar range.

In the scanning mode, collimated light is directed onto a gold coated diffraction grating via a rotatable mirror positioned between the light source and grating that controls the incident angle of the source light without altering the position of the source beam. The scanning mode allows up to approximately one thousand analyses to be run simultaneously.

When the non-scanning SPR mode is selectively employed, rather than a collimated beam impinging upon the grating at a single incident angle, a wedge of light having a range of incident angles (including the resonant angle for all areas of the grating) is directed onto the gold coated diffraction grating. When the instrument is operated in the non-scanning mode, a single image of the gold surface contains sufficient information to construct a series of SPR curves, from which the concentration of analyte on a particular region of interest can be calculated. While the non-scanning mode facilitates kinetic analysis of faster reactions than does the scanning mode, the enabled throughput is reduced to approximately fifty simultaneous analyses.

Figure 1:
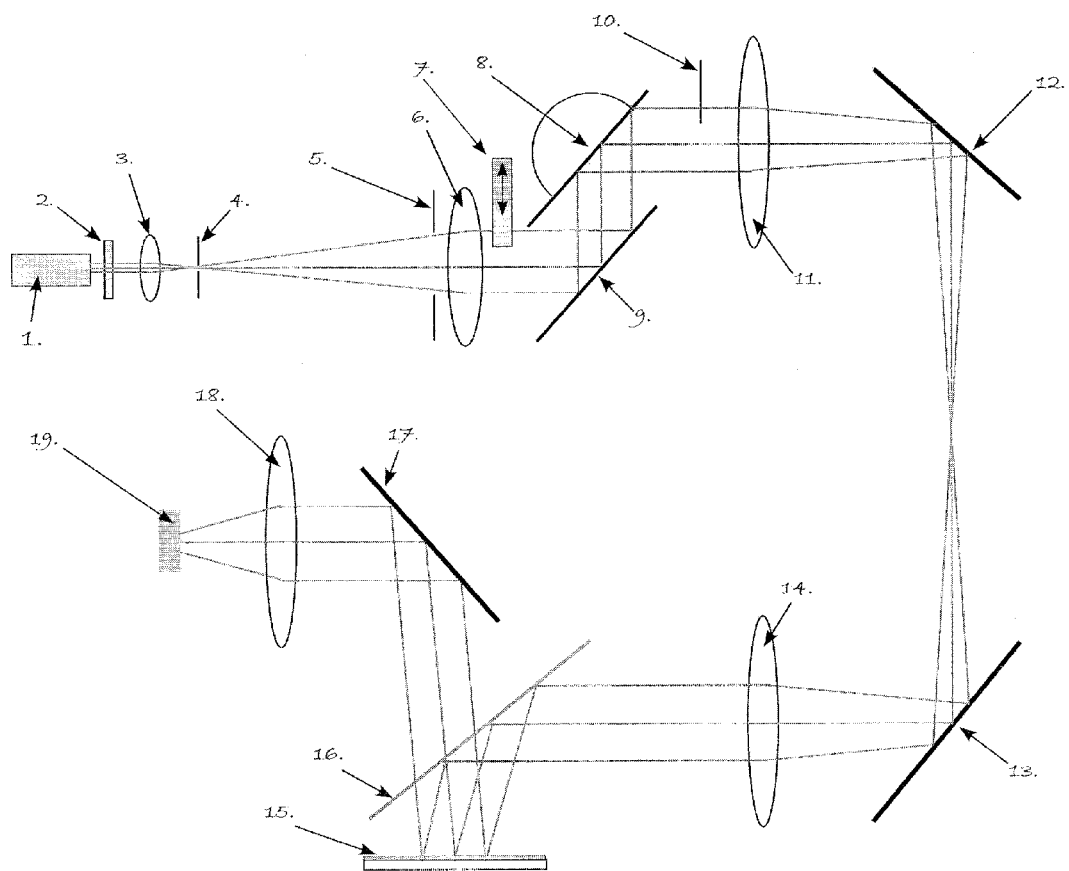
FIG. 1 is a schematic drawing showing the optical path of the instrument in its grating-coupled surface plasmon scanning and non-scanning modes.

FIG. 1 is a schematic diagram of the optics of the instrument in (scanning or non-scanning) GCSPRI mode. As can be seen, the instrument has a light source (1) positioned downstream of various optical components, a grating-coupled surface plasmon resonance chip (15) and a detector (camera) (19). A typical light source (1) that is employed in the instrument is a diode laser that emits light at a wavelength of approximately 635 nm. In the scanning GCSPRI mode, the diode laser is preferably operated at a programmatically selectable low diode current so that it functions as a light-emitting diode. Operating the diode laser in this manner minimizes the formation of interference fringes that would otherwise interfere with a measurement.

During operation in the scanning mode, the light beam from the diode laser is directed through a polarizer (2), and then through a 10× microscope objective (3) that focuses the beam on a spatial filter (4). In a preferred embodiment, the spatial filter (4) comprises a precision 15 µm pinhole diaphragm. Using the pinhole as an approximate point source, the light is collimated at a diameter of approximately one inch by an achromatic doublet (6). In an alternative embodiment, an optical fiber is employed instead of the microscope objective (3) and spatial filter (4) combination. Overfill of the doublet is prevented by means of a stop unit (5). In the FIG. 1 embodiment, the collimated, polarized beam is then directed upward by a first mirror (9) positioned at approximately 45° relative to the beam to a position that will accommodate the SPR chip holder. The first mirror (9) directs the beam to a second mirror (8) that is mounted on a precision rotating stage.

The rotating mirror (8) defines an object plane. An optical telescope formed by lenses (11) and (14) optically connects the object plane with an image plane, transferring polarized light from the object plane to the image plane. In the disclosed instrument, the surface of the chip (15) defines the image plane.

Employment of the telescope in the instrument enables variation in the angle at which light strikes the chip via rotation of the mirror (8). The telescope enables alteration of the incident angle without changing the position of the light beam on the chip. As depicted in FIG. 1, two additional mirrors (12) and (13) fold the light path, enabling the instrument to be packaged more compactly.

As noted earlier, the telescope is positioned with one focus on the sensor surface (image plane) and the other at a mirror (object plane) attached to a precision rotating stage such that the angle of the light striking the sensor surface may be changed without causing the beam to move relative to the position of the sensor. This application of a standard optical telescope configuration allows a source beam to be focused onto the gold-surfaced diffraction grating on the chip (15) so that movement of the relatively small rotatable mirror (8) alters the angle at which the source beam strikes the gold surface without causing the beam to change position relative to the surface. The telescope optics are symmetrical in this embodiment, and thus any modification of the source beam on the object plane is transferred to the image plane at the gold surface of the chip (15) without altering the properties of the light. Placing the desired modification at the opposite focus of the telescope allows the angle at which light is incident upon the chip (15) to be varied while keeping both the light source (1) and chip (15) stationary within the instrument.

A beamsplitter (16) directs a portion of the light onto the GCSPRI chip (15) at the appropriate incident angle. In this embodiment, the beamsplitter (16) is preferably glass. Light reflecting from the GCSPRI chip (15) passes back through the beamsplitter and is reflected by another mirror (17) into a telecentric lens (18). The Telecentric lens (18) focuses an image of the chip into the image sensor (19) of a camera. In a preferred embodiment, the image sensor (19) is a CCD sensor.

In addition to enabling a more compact instrument, the telescope provides an uncongested area removed from the chip that is optically mapped onto the chip. This facilitates the positioning of alternate or additional optical components that can significantly increase the versatility and interchangeability of the instrument, including the selective positioning of a cylindrical lens for the non-scanning mode (described in detail below).

In a preferred embodiment, an opaque member such as a fine wire (10) can be positioned proximate the edge of and extending into the optical path. The wire (10) casts a shadow onto the image on the CCD sensor (19). The image of the wire creates a fiduciary mark that changes position along the edge of the image as a linear function of the angle of the source light. Each image of the chip, therefore, contains a precise indicator of the incident light angle.

The aforementioned non-scanning GCSPRI mode comprises the same optical configuration as the scanning mode, with the additional incorporation of a cylindrical lens (7) that can be selectively shifted into and out of the optical pathway. In one preferred embodiment, the cylindrical lens (7) is mounted on a motor driven slide. Here, the cylindrical lens (7) is positioned between the achromatic doublet (6) and the first mirror (9). Introduction of the cylindrical lens (7) into the optical path causes the collimated light to be focused into a wedge that contains beams impinging on the chip at a range of angles, within which the resonant angle for all positions of the grating is contained. In one embodiment, an additional cylindrical lens can be introduced downstream of the chip (15) for converging the divergent wedge that is reflected from the chip surface (not shown).

When the non-scanning mode is employed, the capture ligands are generally applied as stripes across the center of the chip (15) instead of as a two-dimensional array of spots, as with the scanning mode. The resonant point of each sample stripe occurs at a unique position. Thus, each image of each sample stripe contains sufficient information to determine the resonant angle.

In the non-scanning mode, several images representing a single measurement time are collected. The first image of a series is converted into an array in which each cell represents a pixel of the image. The intensity values of each pixel in each subsequent image are added to the appropriate cell in the array. This pixel-by-pixel averaging method reduces measurement noise in each pixel, and thus improves the overall resolution of the instrument. Due to the arrangement of the capture sites in a single block of rows rather than a two-dimensional array of spots (scanning mode), the non-scanning mode allows analysis of fewer sites than the scanning mode. For example, in a preferred embodiment, approximately fifty capture sites can be analyzed at one time using the non-scanning mode, whereas approximately one thousand capture sites can be analyzed at one time with the scanning mode.

Figure 2:
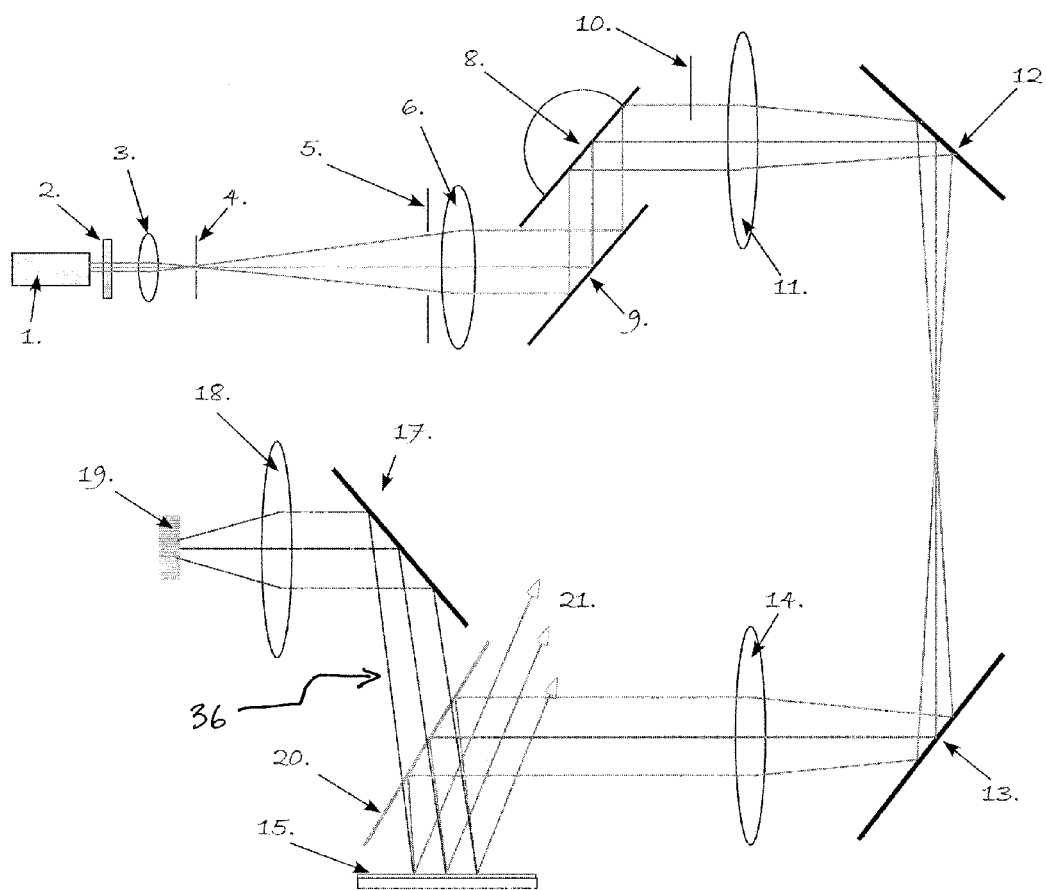
FIG. 2 is a schematic drawing of the optical design of the instrument in the enhanced fluorescence mode.

FIG. 2 is a schematic of the optical path of the instrument's SPR-enhanced fluorescence mode. As indicated by the recurring reference numerals, the optical path is generally identical to the optical path of the scanning GCSPRI mode until the beamsplitter (20) (i.e., input optics). In this embodiment, the diode laser light source (1) is preferably operated at maximum diode current to yield the maximum fluorescence sensitivity. Here, the beamsplitter (20) is dichroic in nature in that it reflects the source wavelength, but allows the longer fluorescence wavelengths emitted from the chip surface to pass.

As depicted, the dichroic beamsplitter (20) is preferably positioned at an angle such that the source excitation light is directed to the chip surface at the reverse of the SPR angle so that the incident excitation light reflected from the surface of the chip is directed away from the detector, as depicted by reference numeral (21). Under these conditions, fluorescence is directionally emitted from the chip at angles that are rather close to the incident angle (see reference numeral (36)). The fluorescence emitted (36) passes through the dichroic beamsplitter (20) and is reflected by another mirror (17) into a telecentric camera lens (18). Any stray reflected excitation light is reflected away from the camera lens by the dichroic beamsplitter. The lens (18) focuses an image of the chip onto the image sensor (19). The fluorescence measurements are improved by removing the incident light from the reading. Like in the aforementioned GCSPRI modes, the preferred image sensor in the fluorescence mode is a CCD sensor.

In the SPR-enhanced fluorescence mode it is desirable to direct as much light as possible onto the fluorophore to increase the sensitivity of measurement. Due to its long coherence length, the laser light can produce undesirable interference fringes when it is directed onto a highly reflective gold surface in close proximity to a glass window. Shifting the rotatable mirror slightly during the exposure time of the camera has the effect of sweeping the fringes across the image, effectively integrating the effects of the fringes and producing a homogeneous background against which fluorescence intensity measurements can be made. Additionally, compensation for spatially distributed systematic intensity bias can be accomplished by subtracting a fluorescence reference image from each measurement image. The fluorescence reference image is generally made by collecting an image of a dilute bulk fluorophore solution in the flowcell that is used to deliver sample to the chip (described in detail below).

In the scanning and non-scanning GCSPRI modes (for which the angle of the source beam is important) the drive current to the diode laser is typically reduced below the laser threshold so that the light source operates as an LED. The reduced coherence length achieved by this adjustment virtually eliminates diffraction fringe interference so that measurements can be made with the rotating mirror fixed during the camera exposure time. In these modes, the intensity of the source illumination can be lower than in the SPR-enhanced fluorescence mode due to the highly reflective gold surface.

In this embodiment of the instrument, the metal-dielectric surface is a glass or plastic nonconducting base upon which a holographic diffraction grating is impressed and covered with a thin layer of gold. The grating pitch and depth can vary and is typically chosen to be compatible with the chosen wavelength of incident light to induce coupling of the incident light to plasmon waves at the gold surface, as is known in the art. That wavelength is also selected to be at the excitation maximum of a group of widely used fluorophores. The wavelength and grating parameters are also chosen to form an overlapping pair of cones of SPR enhanced fluorescence light, emitted at a convenient angle. The wavelength parameters can be chosen by those skilled in the art based upon the other equipment employed and other parameters of the particular instrument.

In one preferred embodiment, incorporation of a gasket and a cover window can convert the gold/dielectric "chip" into a flowcell wherein the engaged chip, gasket and window define a chamber. Holes in the glass cover window allow the chamber to fluidly mate with a fluidic system.

Figure 3:
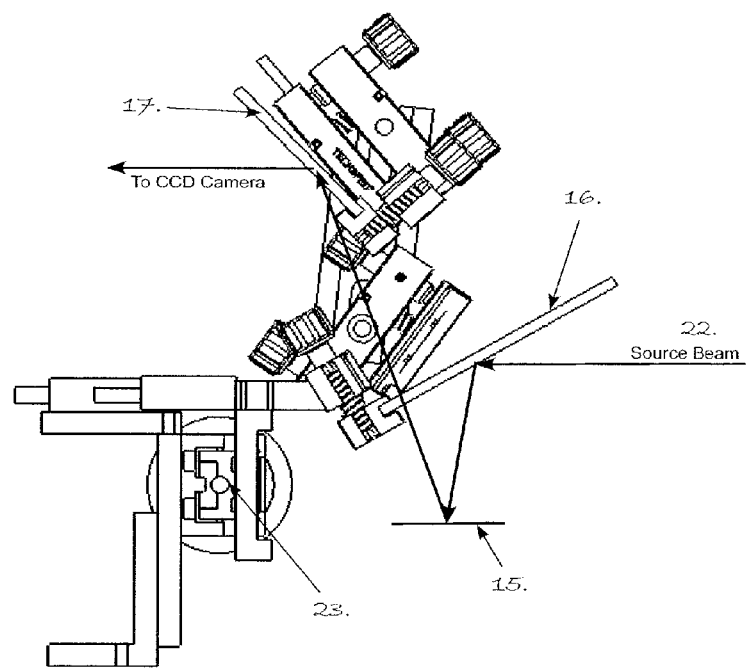
FIG. 3 is a sectional view of the beamsplitter/mirror mount showing the switch between scanning SPR mode and SPR-enhanced fluorescence mode.

With reference to FIG. 3, the GCSPRI modes and the SPR-enhanced fluorescence mode are programmatically selectable by a motor-driven linear slide to which the mirror (17)/beamsplitter (16,20) assemblies of FIGS. 1 and 2 are attached. In FIG. 3, a general light source beam is identified by reference numeral (22). This embodiment depicts the GCSPRI mode beamsplitter (16) and mirror (17), so the light source (22) is acting as an LED. Here, the source beam (22) defines a longitudinal direction. FIG. 3 shows the GCSPRI mode beamsplitter (16) and mirror (17) in position within the optical pathway. The GCSPRI chip (15) generally remains fixed in all operational modes. In this embodiment, to enable the SPR enhanced fluorescence mode, a motor-driven linear slide (23) selectively translates the mirror/beamsplitter assemblies laterally to bring the appropriate mirror/dichroic beamsplitter assembly into the optical pathway and remove the GCSPRI mirror/beamsplitter assembly. The current to the light source is then preferably increased so that the light source beam (22) is a laser. It is notable that the same mirror (17) can be employed in all modes and the different beamsplitters substituted. Of course, the translation method and relative direction thereof is not limiting.

Figure 4:
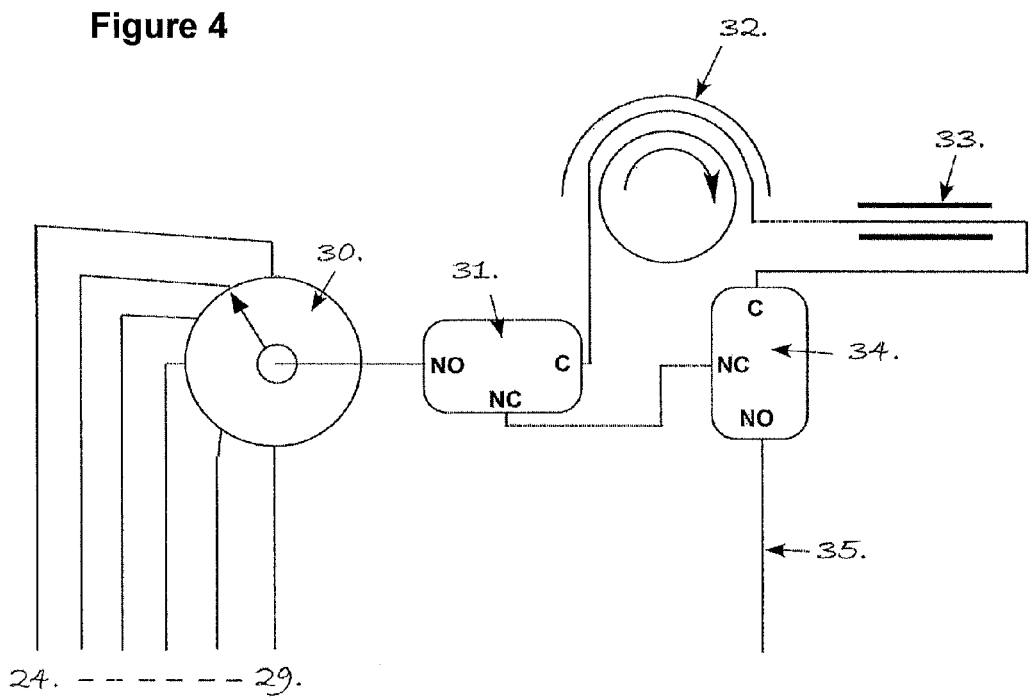
FIG. 4 is a diagram of the fluidics system of the subject instrument.

As noted above, embodiments of the inventive instrument can be equipped with a fluidics system for managing the flow of sample(s) potentially containing analytes. FIG. 4 shows a preferred embodiment of a fluidics system for use within the instrument. Here, the sample input to the instrument comprises a six-way valve (30) with six sample ports (24) through (29). The selected sample passes into a pair of solenoid-activated, programmatically controlled valves (31) and (34) which allow the recirculation of a low volume sample through a sample loop. The sample loop is switched into series with the sample flowcell (33) within which the GCSPRI chip is contained. Fluids exit the system via an outlet port (35). In this embodiment, fluid movement is accomplished by means of a peristaltic pump (32), which provides continuous flow at rates preferably ranging from 1 µl/min to 250 µl/min.

Figure 5:
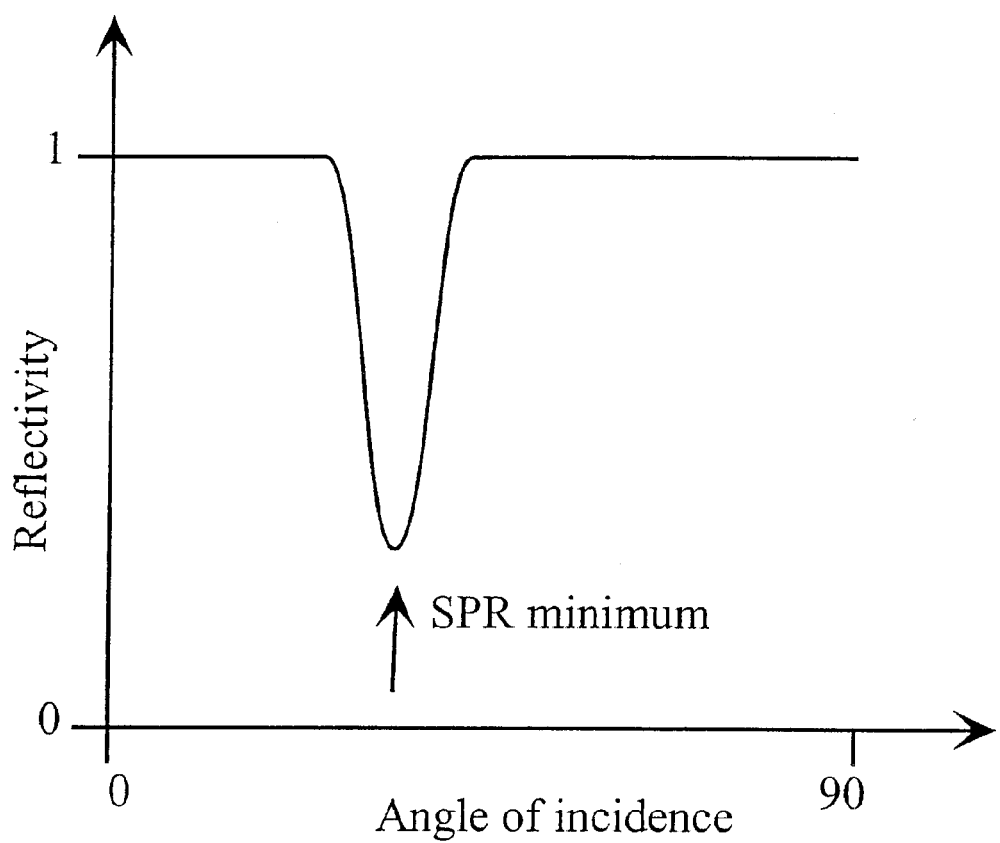
FIG. 5 is a sample SPR curve.

The primary data collected in the scanning and non-scanning GCSPRI modes are a family of SPR curves—one for each capture site plus reference sites for each of numerous points in time. These curves approximate inverted, skewed Gaussian curves. The curves vary somewhat in shape as conditions on the chip change. The curves are collected as a series of discrete values from the pixels of the camera sensor (i.e. the data contain noise as well as systematic error). The preferred output display in GCSPRI mode is a kinetic scan, a plot of the minimum (resonance) angles of the SPR curves as a function of time. Therefore it is important that the minima of the SPR curves be accurately and reproducibly determined to a fraction of a millidegree of light source angle. A sample SPR curve is shown in FIG. 5.

As can be seen, the data for each curve consists of a one dimensional array of intensities (X values) and a matching one-dimensional array of angles (Y values). These data can be input into a LabView curve fitting engine that produces a one-dimensional array of numbers that represent a curve that best fits the experimental data using a fourth order polynomial model. The minimum of the best fit data is then found by truncation and location of the first moment by the method of Equation 1:

$$\langle x \rangle = \frac{\sum S(x_i) x_i}{\sum S(x_i)} \quad \text{[Equation 1]}$$

wherein <x> is a simple and accurate measurement of the center of the peak. Assumptions about the shape of the peak need not be made.

Preferred embodiments of the foregoing invention have been set forth for purposes of illustration. The foregoing descriptions should not be deemed limitations of the invention. Various modifications, adaptations and alternatives may occur to one of skill in the art without departing from the spirit or the scope of the claimed coverage.

What is claimed is:

1. A dual mode optical resonance analysis system comprising:
    a light source operable at a first current to produce collimated, polarized light and a second current to produce laser light;
    an optical system for transmitting light from said light source to a sensor surface along an illumination optical path,
    first and second beam splitters alternatively positionable in said illumination optical path to direct said light upon said sensor surface, said first beam splitter having a first angular orientation selected to direct said light onto said sensor surface at a first range of incident angles so that a majority of light reflected from the sensor surface is incident upon and passes through said first beam splitter, said second beam splitter having a second angular orientation selected to direct light onto said sensor surface at a second range of incident angles so that a majority of light reflected from said sensor surface is not incident upon said second beam splitter,
    an imaging detector to form an image of said sensor surface;
    first and second reflecting surfaces alternatively positionable in a detector optical path from the sensor surface to said imaging detector, said first reflecting surface having a third angular orientation selected to direct light reflected from said sensor surface and passing through said first beam splitter onto said imaging detector, said second reflecting surface having a fourth angular orientation selected to direct light emanating from said sensor surface and passing through said second beam splitter onto said imaging detector,
    wherein in a first mode of operation, said light source is operated at said first current, said first beam splitter and first reflecting surface are positioned in the illumination optical path and detector optical path, respectively, and in a second mode of operation, said light sources is operated at said second current, said second beam splitter and said second reflecting surface are positioned in said illumination optical path and detector optical path, respectively.

2. The dual mode optical resonance analysis system of claim 1, wherein said first beam splitter and said first reflecting surface are arranged to move together as a first set and said second beam splitter and second reflecting surface are arranged to move together as a second set.

3. The dual mode optical resonance analysis system of claim 2, comprising a mechanism for moving said first or second set into position during operation in said first or second mode, respectively.

4. The dual mode optical resonance analysis system of claim 1, comprising a cylindrical lens movable between a first position in said illumination optical path and a second position outside said illumination optical path, said cylindrical lens in said first position refracting light from said light source into a generally rectangular wedge of light containing a range of angles at which said light is incident upon said sensor surface.

5. The dual mode optical resonance analysis system of claim 1, comprising a mechanism for shifting said cylindrical lens between said first and second positions.

6. The dual mode optical resonance analysis system of claim 1, when operating in said second mode, said laser light having a first wavelength excites fluorescence having a second wavelength from fluorophores adjacent said sensor surface, said second beam splitter is dichroic, reflecting said first wavelength away from said detector and passing said second wavelength.

7. The dual mode optical resonance analysis system of claim 1, wherein said sensor surface defines an image plane and said optical system comprises:
    a selectively rotatable reflecting surface defining an object plane, said reflecting surface situated in said illumination optical path;
    an optical telescope optically connecting said object plane to said image plane to transfer said light from said object plane to said image plane, including the angle at which said polarized light is reflected from said object plane,
    wherein rotation of said reflecting surface alters the angle at which said polarized light is incident upon said sensor surface, while said polarized light remains at a substantially fixed position on said sensor surface.

8. The dual mode optical resonance analysis system of claim 1, wherein said light source emits light at a predetermined wavelength appropriate for transferring energy to surface plasmons at said sensor surface and excite fluorescence of molecules thereon.

9. The dual mode optical resonance analysis system of claim 7, wherein said optical telescope comprises first and second substantially identical lenses positioned to transfer light from said object plane to said image plane.

10. The dual mode optical resonance analysis system of claim 7, wherein said optical telescope comprises first and second telescope reflecting surfaces positioned optically between said light source and said sensor surface to fold the illumination light path without altering the properties of the light.

11. The dual mode optical resonance analysis system of claim 6, wherein energy from surface plasmons at said sensor surface is outcoupled to said flurophore, thereby amplifying the fluorescence light emitted by said fluorophore.

12. The dual mode optical resonance analysis system of claim 1, wherein said sensor surface is a dielectric material upon which a holographic diffraction grating is formed and covered with a metallic layer, said diffraction grating having a pitch and depth selected to induce coupling of light to surface plasmons on the metallic surface when light is incident upon said sensor surface at a resonant angle.

13. The dual mode optical resonance analysis system of claim 1, wherein said detector optical path includes a band pass filter when operating in said second mode.

14. The dual mode optical resonance analysis system of claim 7, wherein said rotatable reflecting surface is shifted while light emanating from said sensor surface is being collected by said detector, shifting the angle at which light from said light source is incident upon said sensor surface to integrate any interference fringes caused by said laser light when said system is operated in said second mode, thereby producing a substantially homogeneous background against which measurements of light emanating from said sensor surface are made.

15. The dual mode optical resonance analysis system of claim 6, wherein said detector remains in the same position relative to said sensor surface in said first mode and said second mode of operation said sensor surface is a dielectric material upon which a holographic diffraction grating is formed and covered with a metallic layer having a thickness, said light source is selected to generate light having a predetermined wavelength, the depth and pitch of said diffraction grating and the thickness of said metallic layer are selected so that fluorescence is directionally emitted from said fluorophores in a direction compatible with the position of said detector.

* * * * *